United States Patent [19]
Kissener et al.

[11] Patent Number: 5,567,854
[45] Date of Patent: Oct. 22, 1996

[54] PROCESS FOR SEPARATING MIXTURES OF NITROBENZALDEHYDE ISOMERS

[75] Inventors: Wolfram Kissener, Neunkirchen; Herbert Emde, Köln; Achim Fessenbecker, Heidelberg, all of Germany

[73] Assignee: Bayer Aktiengesellschaft, Leverkusen, Germany

[21] Appl. No.: 532,513

[22] Filed: Sep. 22, 1995

[30] Foreign Application Priority Data

Sep. 29, 1994 [DE] Germany ................. 44 34 848.7

[51] Int. Cl.$^6$ ................................. C07C 45/82
[52] U.S. Cl. .................................. 568/424
[58] Field of Search ............... 568/424; 503/59, 503/62

[56] References Cited

U.S. PATENT DOCUMENTS 4,450,297  5/1984  Preiss et al. ................ 568/424
4,910,345  3/1990  Steicher et al. ............. 568/424

FOREIGN PATENT DOCUMENTS 091575   1/1983   European Pat. Off. ........ 568/424
320539   6/1989   European Pat. Off. ........ 568/424
3212069 10/1963   Germany ..................... 568/424

OTHER PUBLICATIONS

Database WPI, week 91 43, AN 91–312686 (1991).
W. Gerhartz, et al., Ullmann's Encyclopedia of Industrial Chemistry, 5th Completely Revised Edition, vol. A3, p. 470. (1986)

*Primary Examiner*—James H. Reamer
*Attorney, Agent, or Firm*—Sprung Horn Kramer & Woods

[57] ABSTRACT

2- and 3-Nitrobenzaldehydes suitable for use as intermediates for the preparation of pharmaceuticals are obtained in a simple manner and without risk of uncontrolled decompositions by distilling mixtures of nitrobenzaldehyde isomers at bottom temperatures of at most 200° C. in the presence of monomeric and/or polymeric aromatic amines and/or phenols and/or N- and S-containing phenothiazines.

7 Claims, No Drawings

PROCESS FOR SEPARATING MIXTURES OF NITROBENZALDEHYDE ISOMERS

The present invention relates to an advantageous process for separating mixtures of nitrobenzaldehyde isomers by distillation.

In the preparation of nitrobenzaldehyde, e.g. by nitration of benzaldehyde, mixtures arise which contain 2-, 3- and 4-nitrobenzaldehyde. For the further use of nitrobenzaldehyde, in particular for the preparation of pharmaceutical active compounds, it is necessary to have available products as isomer-free as possible, e.g. 2-nitrobenzaldehyde and 3-nitrobenzaldehyde as pure as possible.

A separation of mixture of nitrobenzaldehyde isomers by direct distillation is not possible since even in the case of a procedure employing reduced pressure, temperatures are necessary which lead to uncontrollable decompositions. In Ulmann's Encyclopedia of Industrial Chemistry, 5th edition, volume A3, p.470 (1985) an explicit warning is given of the danger of explosions if crude mixtures containing 3-nitrobenzaldehyde are distilled under reduced pressure.

Therefore, in the process which has hitherto been the best industrially for the preparation of 2-nitiobenzaldehyde, a mixture of isomers containing 2-nitrobenzaldehyde is first converted into the corresponding acetals, then 2-nitrobenzaldehyde acetal is separated off by distillation from the acetal mixture and finally the 2-nitrobenzaldehyde acetal separated off is cleaved again, releasing 2-nitrobenzaldehyde (see German Offenlegungsschrift 3212069). This process yields sufficiently pure 2-nitrobenzaldehyde, but it is complex because of two additional reaction stages (acetal formation and acetal cleavage).

An improved process has now been found for separating mixtures of nitrobenzaldehyde isomers, which is characterized in that mixtures of nitrobenzaldehyde isomers are distilled at bottom temperatures of at most 200° C. in the presence of monomeric and/or polymeric aromatic amines and/or phenols and/or N- and S-containing phenothiazines.

Any desired mixtures of nitrobenzaldehyde isomers can be used in the process according to the invention, e.g. those which contain 2 or 3 isomers. These mixtures can be of any origin. Preferably, mixtures of nitrobenzaldehyde isomers are used such as arise in the nitration of benzaldehyde. Such mixtures typically contain 19 to 23% by weight of 2-nitrobenzaldehyde, 75 to 80% by weight of 3-nitrobenzaldehyde and 1 to 3% by weight of 4-nitrobenzaldehyde. Such mixtures may or may not contain still further components, e.g. 1 to 5% by weight of water and/or traces of sulphuric acid, benzaldehyde, nitrobenzene and/or nitrobenzoic acids.

Preferably, 2-nitrobenzaldehyde is distilled off in the process according to the invention or 2- and 3-nitrobenzaldehyde are distilled off sequentially. The monomeric and/or polymeric aromatic amines and/or phenols to be used according to the invention, below also termed stabilizers, can be used, e.g. in amounts of 0.5 to 2% by weight, based on the mixture of nitrobenzaldehyde isomers used. Higher dosages are possible, but do not bring further advantages. Stabilizer additions of less than 0.5% by weight are not generally sufficiently effective.

Aromatic amines which can be used as stabilizers are, e.g., pyridine, diphenylamine, dihydroquinoline and naphthylamine and derivatives thereof, e.g. those derivatives which contain phenyl, $C_1$–$C_4$-alkyl and/or $C_1$–$C_4$-acyl groups. Substituted and unsubstituted aromatic amines may, if appropriate, be polymerized.

The following may be mentioned as individual examples: pyridine, 2-phenyl pyridine, polymerized trimethyldihydroquinoline, N-phenyl-α-naphthylamine and acetylated diphenylamine. Phenols which may be used as stabilizers are, e.g., cresols and 2,2'-methylenebisphenols and derivatives thereof, e.g. those derivatives which contain straight-chain, branched and/or cyclic alkyl radicals having up to 8 C atoms. Substituted and unsubstituted phenols may, if appropriate, be polymerized. Individual examples which may be mentioned are: 2,2'-methylenebis-(4-methyl-6-tert-butylphenol), di-tert-butylcresol and 2,2'-methylene-bis-(4-methyl-6-cyclohexylphenol).

S- and/or N-containing, preferably sterically hindered, aromatic phenols or N- and S- containing phenothiazines can also be used.

Stabilizers which can be used in the process according to the invention are, e.g., commercially available in the form of various Vulkanox® types.

Preferably, the process according to the invention is carried out at bottom temperatures in the range 150° to 190° C. and at top temperatures of 110 to 135° C. This means that the distillation must be carried out at reduced pressure, for example at 1 to 30 mbar.

The distillation can be carried out continuously or batchwise. A column is expediently used here, for example a packed column.

The stabilizers to be added can, for example, be added to the molten mixture of nitrobenzaldehyde isomers to be used. The stabilizers remain in the bottom product after distillation and can be reused if appropriate.

In the manner according to the invention, 2- and 3-nitrobenzaldehydes suitable as intermediate for pharmaceuticals can be obtained in a simple and advantageous manner without the necessity of converting them into an acetal intermediate and without the risk of uncontrollable decompositions.

This is extremely surprising, since the stabilizers to be used are otherwise used as antioxidants in rubber chemistry. However, in the distillation of nitrobenzaldehydes, it is not oxidisation reactions which cause uncontrollable decompositions, but a disproportionation of the aldehyde groups.

By our own studies it was established that carrying out the distillation of mixtures of nitrobenzaldehyde isomers under nitrogen does not decrease the risk of uncontrollable decompositions.

EXAMPLE 1

47 g of a mixture which contained 9.74 g of 2-nitrobenzaldehyde, 2% by weight of water and further, in addition, 3- and 4-nitrobenzaldehyde received an addition of 1.0 g of styrenated diphenylamine and the mixture was distilled with stirring in a distillation apparatus of 22 mbar and 180° C. bottom temperature (bath temperature). In the distillate, 9.35 g of 2-nitrobenzaldehyde were found by analysis (GC). This corresponds to 96% by weight of the starting amount.

EXAMPLE 2

(To illustrate that the risk of uncontrollable decompositions no longer exists in the process according to the invention)

A mixture of isomers which contains 2-, 3- and 4-nitrobenzaldehyde and 2.5% by weight of water was weighed out into a sample tube and measured in a heat flux calorimeter. At a heating rate of 3K/min, there was a marked exothermic process, beginning at approximtely 180° C. and having a maximum at approximately 210° C.

Repetition of this measurement with the same mixture of isomers which, however, contained 2% by weigh of polymeric trimethyldihydroquinoline showed that the exothermic process then began at approximately 230° C. and had the maximum at approximately 280° C.

What is claimed is:

1. A process for separating mixtures of nitrobenzaldehyde isomers, which comprises to distill mixtures of nitrobenzaldehyde isomers at bottom temperatures of at most 200° C. in the presence of one or more members of the group consisting of monomeric aromatic amines, polymeric aromatic amines, phenols and N- and S-containing phenothiazines.

2. The process of claim 1, which comprises to distill mixtures of nitrobenzaldehyde isomers which contain 2 or 3 isomers.

3. The process of claim 1, which comprises to distill mixtures of nitrobenzaldehyde isomers which arise in the nitration of benzaldehyde.

4. The process of claim 1, which comprises to use 0.5 to 2% by weight of one or more members of the group consisting of monomeric aromatic amines, polymeric aromatic amines and phenols, based on the mixture of nitrobenzaldehyde isomers used.

5. The process of claim 1, which comprises to use aromatic amines selected from the group consisting of polymerized pyridine, unpolymerized pyridine, diphenylamine, dihydroquinoline, naphthylamine and derivatives thereof which contain phenyl, $C_1$–$C_4$-alkyl or $C_1$–$C_4$-acyl groups.

6. The process of claim 1, which comprises to use phenols selected from the group consisting of cresols, 2,2'-methylene-bis-phenols and derivatives thereof which contain straight-chain, branched cyclic alkyl radicals having up to 8 C atoms.

7. The process of claim 1, which comprises to employ bottom temperatures in the range 150° to 190° C., top temperatures in the range 110 to 135° C. and pressures in the range 1° to 30 mbar.

* * * * *